United States Patent
Dehnert et al.

(10) Patent No.: US 6,498,341 B2
(45) Date of Patent: Dec. 24, 2002

(54) METHOD FOR CHARACTERIZING GROUND WATER MEASUREMENT POINTS BY DISTINGUISHING GROUND WATER FROM SUBTERRANEAN WATER ACCUMULATION

(75) Inventors: Joerg Dehnert, Berggiesshübel (DE); Klaus Freyer, Holzhausen (DE); Wolfgang Nestler, Dresden (DE); Hanns-Christian Treutler, Naunhof (DE)

(73) Assignee: UFZ-Umweltforschungszentrum Leipzig-Halle GmbH (DE)

( * ) Notice: Subject to any disclaimer, the term of this patent is extended or adjusted under 35 U.S.C. 154(b) by 0 days.

(21) Appl. No.: 09/809,679

(22) Filed: Mar. 15, 2001

(65) Prior Publication Data

US 2001/0019106 A1 Sep. 6, 2001

Related U.S. Application Data

(62) Division of application No. 09/180,706, filed as application No. PCT/EP97/02450 on May 14, 1997, now Pat. No. 6,252,598.

(30) Foreign Application Priority Data

May 14, 1996 (DE) .......................... 196 21 158
Mar. 16, 1997 (DE) .......................... 197 11 110

(51) Int. Cl.⁷ .......................... G01N 33/18; E21B 47/01
(52) U.S. Cl. .......................... 250/255; 250/256
(58) Field of Search .......................... 250/255, 259, 250/260, 303, 256; 73/53.01, 152.23, 152.29, 152.42

(56) References Cited

U.S. PATENT DOCUMENTS

| | | | |
|---|---|---|---|
| 4,844,839 A | * | 7/1989 | Manchak, Jr. et al. ........ 588/17 |
| 5,224,389 A | * | 7/1993 | Jensen et al. ............ 73/863.01 |
| 5,744,730 A | | 4/1998 | Ballard et al. |
| 6,021,664 A | | 2/2000 | Granato et al. |

FOREIGN PATENT DOCUMENTS

| | | | |
|---|---|---|---|
| DE | 282 770 | 9/1990 | |
| DE | 39 11 366 | 10/1990 | |
| DE | 42 17 236 A1 | * 12/1993 | ............ G01N/1/22 |
| DE | 297 04 842 | 5/1997 | |
| JP | 06 324200 | 11/1994 | |

OTHER PUBLICATIONS

Hoehn E., et al; "Radon in Groundwater: a Tool to Assess Infiltration from Surface Waters to Aquifiers" Water Resources Research, Aug. 1989; Bd. 25, No. 8, ISSN 0043–1397, see pp. 1795–1803.

(List continued on next page.)

Primary Examiner—Constantine Hannaher
Assistant Examiner—Albert Gagliardi
(74) Attorney, Agent, or Firm—Norris, McLaughlin & Marcus P.A.

(57) ABSTRACT

The invention describes a method and apparatuses for characterizing groundwater measuring sites by differentiating between groundwater and static water and serves, for example, for determining the pumping-out times of groundwater measuring sites, optimum for investigations of the representative nature, as well as for identifying and localizing defects at groundwater measuring sites. The invention is based on measuring the radon activity concentration or the total activity concentration of the groundwater samples. The measurement of the concentrations by offline or online methods permits the ratio of groundwater to static water in a groundwater measuring site to be determined reliably. A novel flow-through measurement cell, as well as a borehole probe are described The invention can be employed wherever investigations of the nature of groundwater are carried out.

3 Claims, 5 Drawing Sheets

OTHER PUBLICATIONS

Willme U. et al.; Bestimmung von Grundwasserverweilzeiten mit Geogenem 222Radon Bei Kunstlicher Grundwasseranreicherung und Ulferfiltration in Einer Trinkwassergewinnungsanlage GWF Wasser Abwasser, Bd. 136, No. 5, May 1, 1995, see pp. 234–241.

Labed V. et al; "Study of $^{222}$Rn Permeation Through Polymer Membranes: Application to Continuous Measurement of $^{222}$Rn in Water" Health Physics, Aug. 1992; Bd. 63, No. 2, ISSN 0017–9078, see pp. 172–178.

* cited by examiner

Fig. 4

METHOD FOR CHARACTERIZING GROUND WATER MEASUREMENT POINTS BY DISTINGUISHING GROUND WATER FROM SUBTERRANEAN WATER ACCUMULATION This is a divisional application of application 09/180,706 filed Nov. 13, 1998 and issued into U.S. Pat. No. 6,252,598, which is a 371 application of PCT/EP97/02450 filed on May 14, 1997, claiming priority of German Applications 196 21158.1 filed on May 14, 1996 and 197 11 110.6 filed on Mar. 16, 1997.

BACKGROUND OF THE INVENTION

1. Field of the Invention

The invention relates to a method and apparatuses for characterizing groundwater measuring sites by differentiating between groundwater and static water by determining groundwater parameters at measuring sites and can be used for the on-site determination of the optimum sampling time, for the determination of the pumping-out times optimum for-investigations of the representative condition and for monitoring groundwater measuring sites for defects. The invention can be used, in particular, within the scope of investigating the condition of groundwater.

The protection of groundwater for producing drinking water, as well as the checking of suspected abandoned polluted areas, the investigation of abandoned polluted areas and the clean-up of damage make it necessary to obtain a constantly increasing number of groundwater samples. Groundwater observation pipes and groundwater measuring sites were and are being set up in order to sample the groundwater. At the same time, the analytical methods for determining the components of the water were refined and the spectrum of individual materials detectable was expanded. Both led to new demands for the quality of groundwater samples. The high requirements of analysis and the financial expense involved in obtaining groundwater samples likewise require a careful depth-oriented and representative sampling. A prerequisite for this is the correct selection of measurement site type, sampling techniques and sampling technology. Moreover, for ensuring that a groundwater sample is representative, it is necessary to know the optimum pumping-out time. If a sample, because the pumping-out time selected has been too short, contains larger amounts of static water from the groundwater observation pipe, the evaluation of the results of analysis can lead to wrong conclusions. On the other hand, excessively long pumping-down times can attract water bodies from other levels, which is also undesirable. The correct determination of pumping-down times for groundwater observation pipes is a problem, which heretofore has not been solved completely.

Before any sample is taken, the groundwater observation pipe, which is to be sampled, must be pumped out until the pumped water corresponds to that of the surrounding groundwater and is no longer influenced by the measuring site. In this connection, it is known that the pumping out should be continued until the electrical conductivity, the temperature and the pH reach constant values. At the same time, it is known that the electrical conductivity is only an orienting parameter. Further known methods, such as the repeated exchange of the contents of the pipe, are rules of thumb. In summarizing, it can be surmised that the constancy of the electrical conductivity is the generally employed criterion at the present time for determining the time for taking a representative sample, although only little is known about the processes, which cause the decrease in electrical conductivity in a ground water observation pipe.

It is a disadvantage of this method that, although the constancy must be regarded as a necessary conditions for a subsequent sampling, it is not a sufficient condition, since the electrical conductivity can reach a plateau value even before the time, at which a representative sample can be taken. This occurs, for example, when the ground water observation pipe has already been sampled days or weeks before the sample is taken. On the other hand, the radon activity concentration can be taken as a reliable criterion, even if only a few days have elapsed between the two samplings. Moreover, the relative change between the initial value (static water) and the final value (groundwater) generally is several times smaller for conductivity than for the radon activity concentration, which makes it easier to establish the optimum time for taking representative samples when the radioactivity concentration is used.

2. Description of the Related Art

Such a method for determining the optimum pumping out times of groundwater observation pipes for establishing an optimum time for sampling is known from DE 3911366 C2. For this method, the conductivity of the water is monitored and representative sampling is initiated when the conductivity is constant Furthermore, the DE 42 17 263 A1 discloses a method, with which gaseous components are also monitored for the sampling. However, this method is concerned not with using gas for establishing the sampling time but with a method of gas sampling, which is similar to the groundwater sampling.

Finally, from the literature references, Health Physics, vol. 53 (1987), pages 181–186 and Radioisotopes, vol. 30 (1981), pages 649–654, methods are known for measuring radon in air (unsaturated zone, ground air) by the LSC method. For this method, radon-containing air is blown with an inlet tube into stationary water in order to dissolve in the water. It can then be extracted from the water once again with an LSC cocktail and measured.

SUMMARY OF THE INVENTION

The invention is based on the objective of providing a method for characterizing groundwater measuring sites by differentiating between groundwater and static water and for determining the optimum pumping-out times of the groundwater observation pipes, which method is optimum for investigating the condition and permits the optimum pumping-out time to be determined reliably and reproducibly with high accuracy at a cost that is justifiable and ensures a reliable determination of the ratio of groundwater to static water in a groundwater sample, as well as the localization of defects.

Pursuant to the invention, this objective is accomplished by the distinguishing features in the characterizing part in claim 1. Appropriate developments of the invention are contained in the dependent claims.

A special advantage of the invention consists therein that the optimum pumping-out times and the optimum times for the sampling are determined with very high accuracy and reproducibility, in that water samples are taken at defined, consecutive times during the pumping-out process, the radon activity concentration of the samples taken is measured and the attainment of a radon activity concentration, which remains essentially constant, signals the optimum time for representative sampling.

A further advantage of the invention lies therein that the groundwater measuring site parameters can be determined without a delay of time, in that the radon activity concentration and/or the total activity concentration are determined and evaluated spectrometrically and/or by diffusion into an air volume or degassing by subsequent measurement in situ directly from the groundwater that is to be investigated.

BRIEF DESCRIPTION OF THE DRAWINGS

The invention is to be described in greater detail below by means of examples, some of which are shown in the drawing, in which.

DESCRIPTION OF THE PREFERRED EMBODIMENTS

Figure 1:
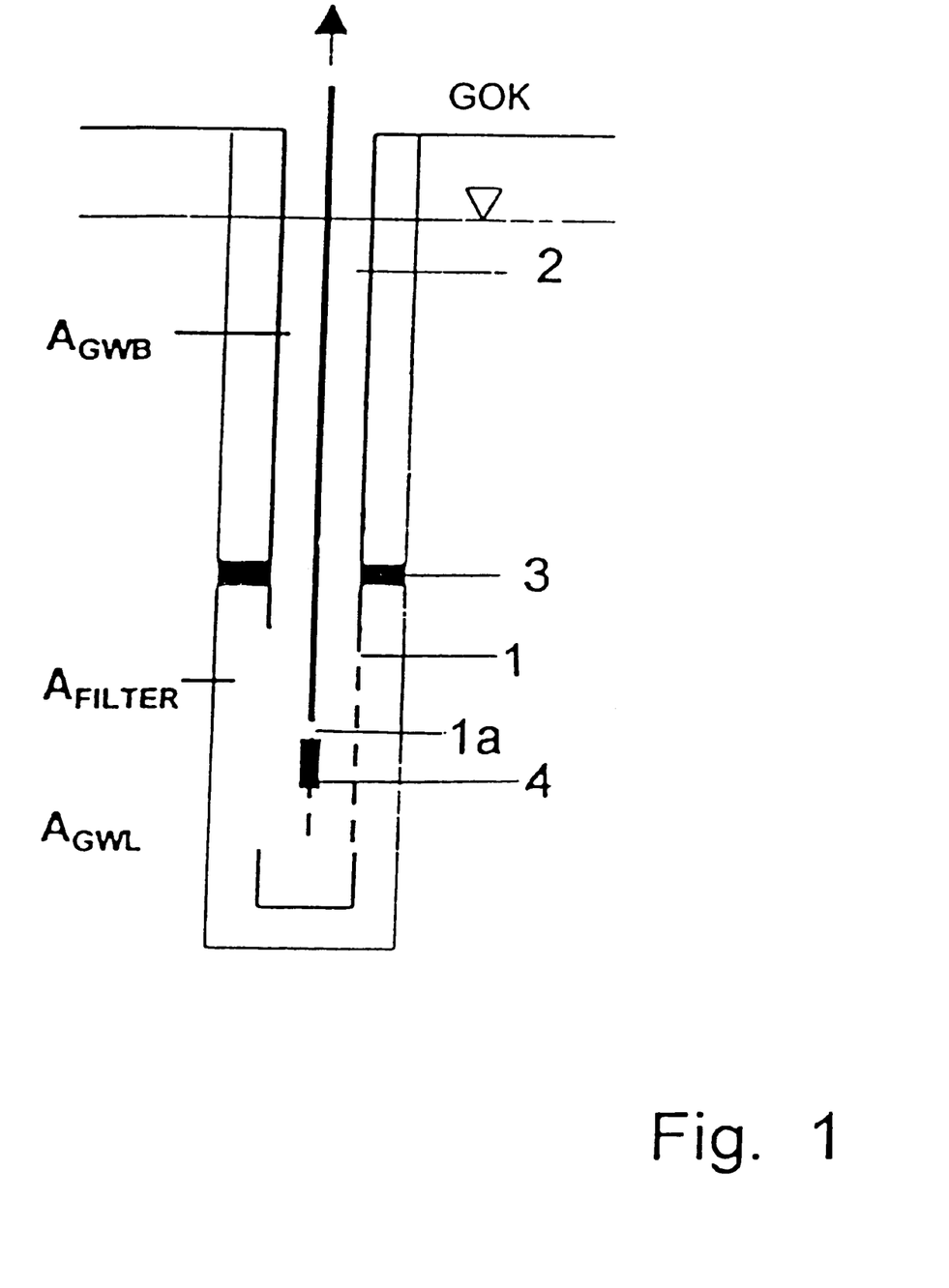
FIG. 1 shows the distribution of the radon activity concentration at a groundwater observation pipe.

As can be seen from FIG. 1, three different radon activity concentrations occur in the groundwater in the region of a groundwater observation pipe. The grain framework of the aquifer produces a basic activity $A_{GWL}$. The incorporated filtering gravel 1 of foreign origin and larger grain diameter produces its own radon activity concentration $A_{Filter}$. The activity $A_{GWBR}$ in the non-filtered standpipe 2 of the groundwater observation pipe, on the other hand, is zero. Water flows through the pore space of the filtering gravel 1 below the clay obstruction 3 and through the filter pipe 1a of the groundwater observation pipe with the activity $A_{GWL}$. Depending on the flow velocity of the groundwater and the amount of filtering gravel 1 incorporated, the activity of the groundwater dominates also in the filtering gravel 1 and in the interior of the filter pipe 1a. On the other hand, no radon is formed in the unfiltered standpipe (upper portion of casing of drainage well) 2 of the groundwater observation pipe. The activity of the water in the standpipe 2, through which there is no flow, therefore falls to the value zero, in accordance with the equation for the radioactive decay:

$$A_t = A_e x e^{-\lambda t} \quad (1)$$

in which $A_t$=radon activity at time t $A_e$=radon activity at equilibrium $\lambda$=radioactive decay constant, $1_{gn}$=0.18 d$^{-1}$ This means that, when groundwater, with an activity of $A_{GWL}$, is pumped by a sampling procedure into the standpipe 2, an activity of only 1% of the initial value can be measured after a period of 26 days has elapsed, because of the short half-life time of the radon. With that, radon is an ideal parameter for determining the proportion of static water in a groundwater sample. If the radon activity concentration of the water, which is pumped away, is measured, then this activity commences at zero and approaches a plateau value corresponding to the mixing ratio of groundwater and static water. By means of such a curve, the time for a representative sampling can be determined exactly as a function of the exchange volumes of the groundwater observation pipe. For all investigations of the pumping-out behavior of a groundwater observation pipe, the two different possibilities of installing the pump in the filter region or directly below the groundwater observation area must be considered separately. The pump 4 can be installed one meter below the upper edge of the filter or in the center of the filter or, if the groundwater observation pipes are deep and the pump technology required for such pipes is lacking, the pump 4 can be installed one meter below the groundwater surface. Continuously filtered groundwater observation pipes are excluded from the following considerations.

Radon is a radioactive noble gas and has three isotopes with mass numbers of 219, 220 and 222. They are products of the natural decay series of $^{238}$U, $^{232}$Th and $^{235}$U. The occurrence and distribution of the three radioisotopes in water is determined by their half-life times. If they are too short, the isotopes decompose at the site of their formation. Accordingly, thoron ($^{220}$Rn), with a half-life time of 56 seconds, and actinon ($^{219}$Rn), with a half-life time of 4 seconds, reach the moved liquid phase hardly or not at all. Radon-222, with a half-life time of 3.8 days, and its decay products are therefore the main sources of natural radiation in groundwater. Radon-222 (referred to in the following as radon) is formed from radium-226, a decay product of $^{238}$U. The decay products of radon are isotopes of the elements polonium, bismuth and lead. The decay of radon to $^{214}$Po takes place through three alpha and two beta decays. The equilibrium between radon and its decay products is attained after about 3 hours. Especially due to recoil effects, radon emerges during alpha decay from solid and loose rock or reaches the liquid phase through diffusion at the grain surface. Because of the short half-life time, this is followed by a limited transport process due to diffusion and groundwater flow (migration). The grain structure of the aquifer permanently produces radon and releases this to the liquid phase. The emanation rate from loose rock depends on the concentration of the precursor isotope radium-226 as well as on the particle size and on the shape of the grain surface. The radon activity concentration of the groundwater, moreover, correlates with the stratigraphy of the aquifer.

Figure 2A:
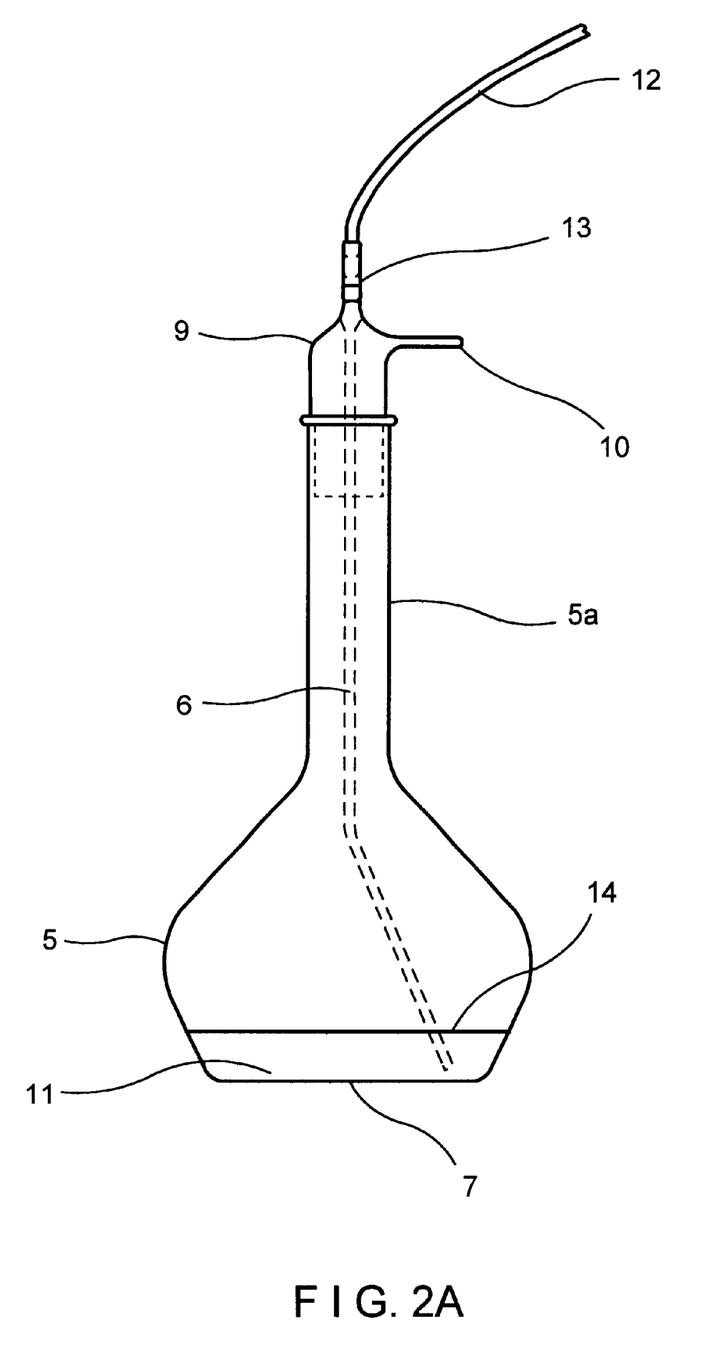
FIG. 2A shows a diagrammatic representation of the sampling vessel with inlet pipe.
Figure 2B:
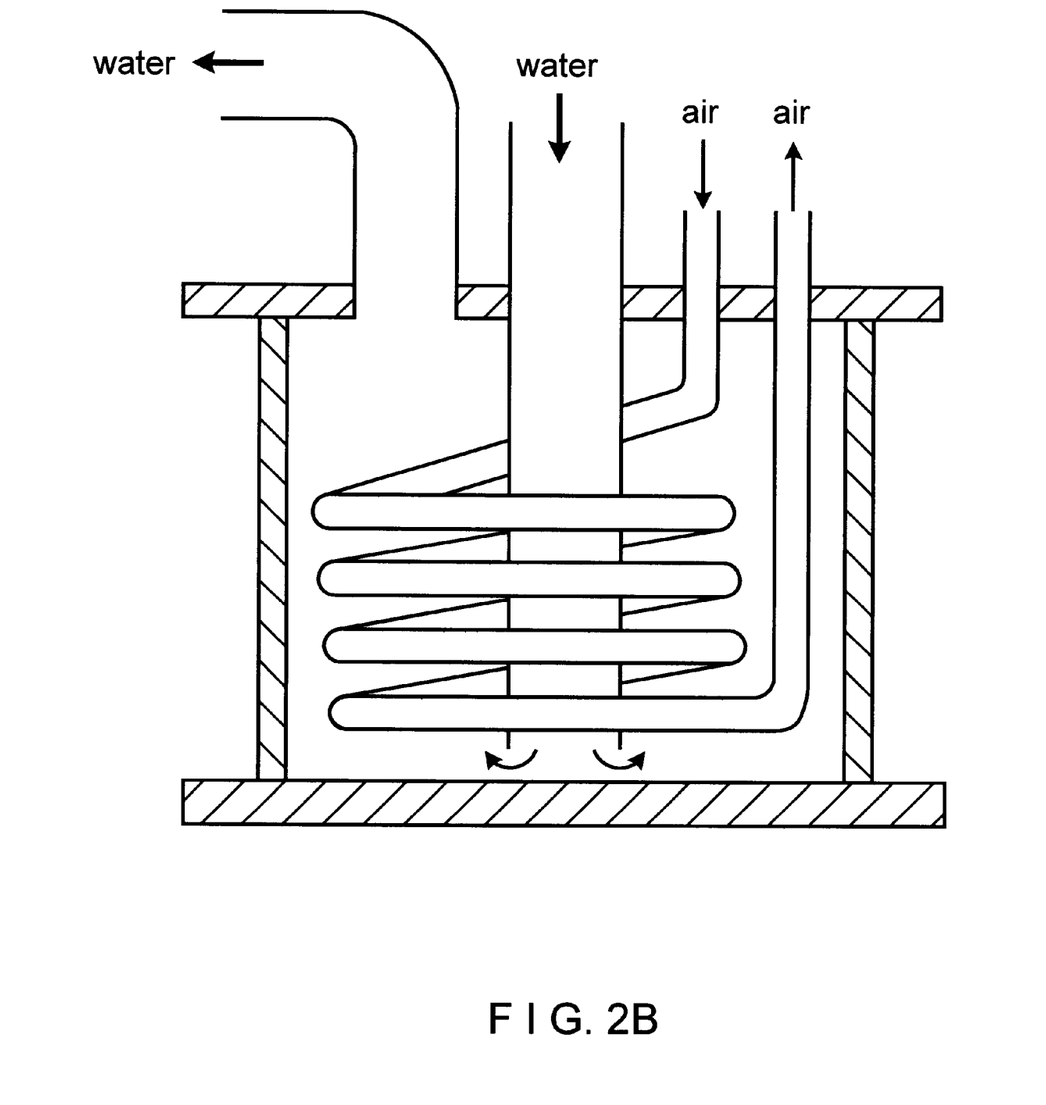
FIG. 2B shows a diagrammatic representation of a borehole probe for radon activity concentration in static water.

In the following the sampling vessel 5, shown in FIG. 2, as well as the measuring technology are described in greater detail. The sampling vessel 5 is constructed so that the very mobile radon cannot escape during the filling and the subsequent transport. Above all, the water sample must not come into contact with air. When the sampling vessel 5 is being filled, the groundwater sample 11 is layered with little turbulence below the cocktail 14. In order to achieve this, an inlet tube 6 is disposed with a ground glass core in an attachment 9, which also has a venting tube 10, the inlet tube 6 extending into the sampling vessel 5 as far as a short distance above the bottom 7 of the sampling vessel and the end of the inlet tube 6 being below the surface of a toluene scintillator. At the start of the sampling procedure, the sampling vessel 5 is held inclined in such a manner, that the cocktail 14 collects at the end of the inlet tube 6. At the same time, it is ensured that there is a sufficient layer above the inflowing groundwater sample even during the initial turbulence. In the present example, the sample volume amounts to one liter. After the sampling procedure, the inlet tube 6 is removed from the sampling vessel 5 and the sampling vessel 5 is closed off tightly with a polyethylene stopper. In addition, Teflon seals are placed between the stopper and the neck 5a. Because radon is several times as soluble in the toluene scintillator cocktail than in water, the cocktail 14, floating in the narrow neck 5a of the sampling vessel 5, forms a reliable protection against loss of radon during the transport of the sample.

In order to avoid radon losses already during the sampling procedure and, at the same time, make the sampling conditions more objective, the attachment 9 with the venting tube 10 and the inlet tube 6 with a ground core are made of glass. The cocktail 14 is added to the sampling vessel 5 already before the sampling procedure and the groundwater sample 11 is placed below the cocktail with the help of the inlet tube 6. The groundwater sample 11 is passed over a bypass and a polyethylene tube 12 when an underwater pump 4 is used and over a direct coupling of the polyethylene tube 12 over a tube coupling 13 when membrane pumps are used through the inlet tube 6 directly under the cocktail 14 without contacting air. To protect the glass inlet tube 6 against damage, a second tube coupling can be used in such a way, that the inlet tube 6 remains firmly connected with a piece of tubing over the tube coupling 13 and the polyethylene tubing 12 is coupled and separated over a second tube coupling. The sampling thus takes place with little turbulence and without bubbles.

The water sample, obtained with the underwater motor pump 4, is pumped over a bypass and an inlet pipe without bubbles and without contact with air into a 1 liter measuring flask 5. In this measuring flask 5, there are 20 mL of a toluene scintillator (cocktail, toluene scintillator made by Packard, 5 g of PPO and 0.1 g of POPOP per liter of toluene), below which the groundwater sample is layered. In the laboratory, the radon is extracted by shaking the measuring flask 5 and the cocktail, pipetted off, is transferred into vials. The vials are measured in a Packard TRI-CARB 2550 TR/AB liquid scintillation spectrometer. The alpha/beta discrimination can be used to evaluate the correctness of the results of the measurements. The radon concentration at the time of the sampling is measured by regression from repeated measurements of a vial. The radon concentrations, determined in the liquid scintillation spectrometer, are expressed in cpm (counts per minute).

Measurement probes and a flow-through measurement cell are used to measure the electrical conductivity and optionally the pH and the temperature. The pumped stream of groundwater is divided over a bypass into two partial streams for obtaining the groundwater samples and for flowing through the flow-through measurement cell. During the sampling, the pumped stream is not restricted, since the radon activity concentration is independent of the pumped stream.

In the following, two pumping-out experiments are explained in greater detail. The two sampled groundwater observation pipes were of equal construction. They had a pipe diameter of 4.5" and a hole diameter of 13" and were equipped with a 1 m long stainless steel, wound filter. The grain size of the filtering gravel was 2–8 mm and the porosity was assumed to be 0.25. In the following, the exchange volume is defined as the capacity of the groundwater observation pipe, including the pre space of the gravel filtering fill.

Figure 3:
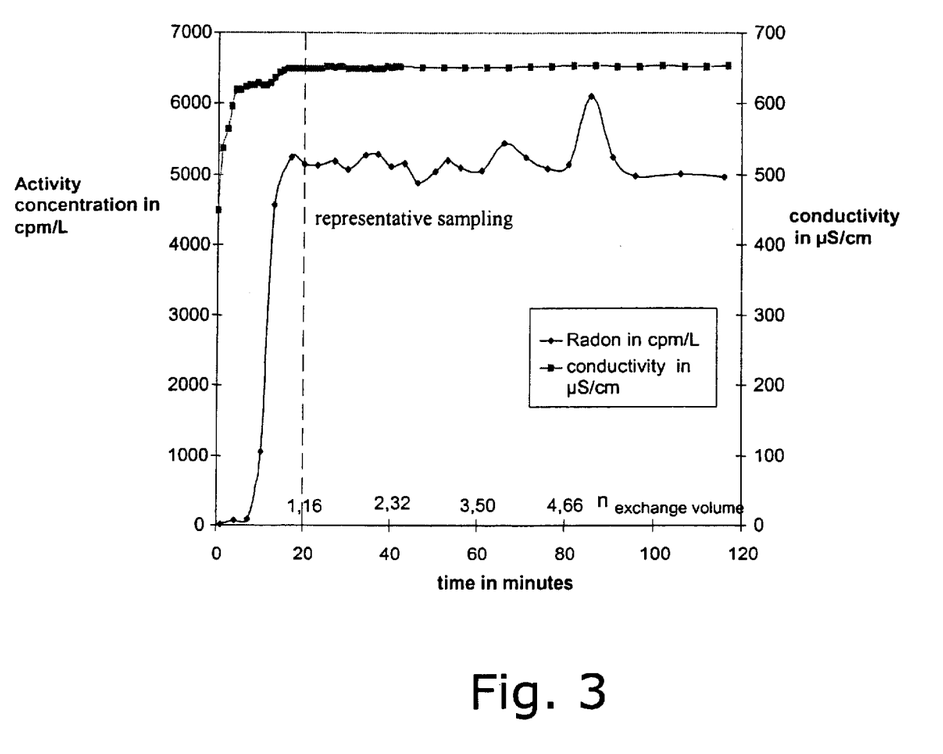
FIG. 3 shows a diagram of the measured radon activity concentration and electrical conductivity during a pumping-out experiment with the pump directly under the groundwater surface and FIG. 4 shows a diagram of the measured radon activity concentration and electrical conductivity during a pumping-out trial with the pump in the filter region.

In experiment A, the pump 4 was installed one meter below the surface of the groundwater (installed depth 6 m) in the groundwater observation pipe with a vertical water column up to the lower edge of the filter of 39 m. The filtering gravel fill was 5.5 m thick. At a constant pumping rate of 1.75 m$^3$/h, samples for determining the radon activity concentration were taken at three minute intervals. At the same time, the electrical conductivity was recorded every minute. The experiment lasted 120 minutes (FIG. 3).

Figure 4:
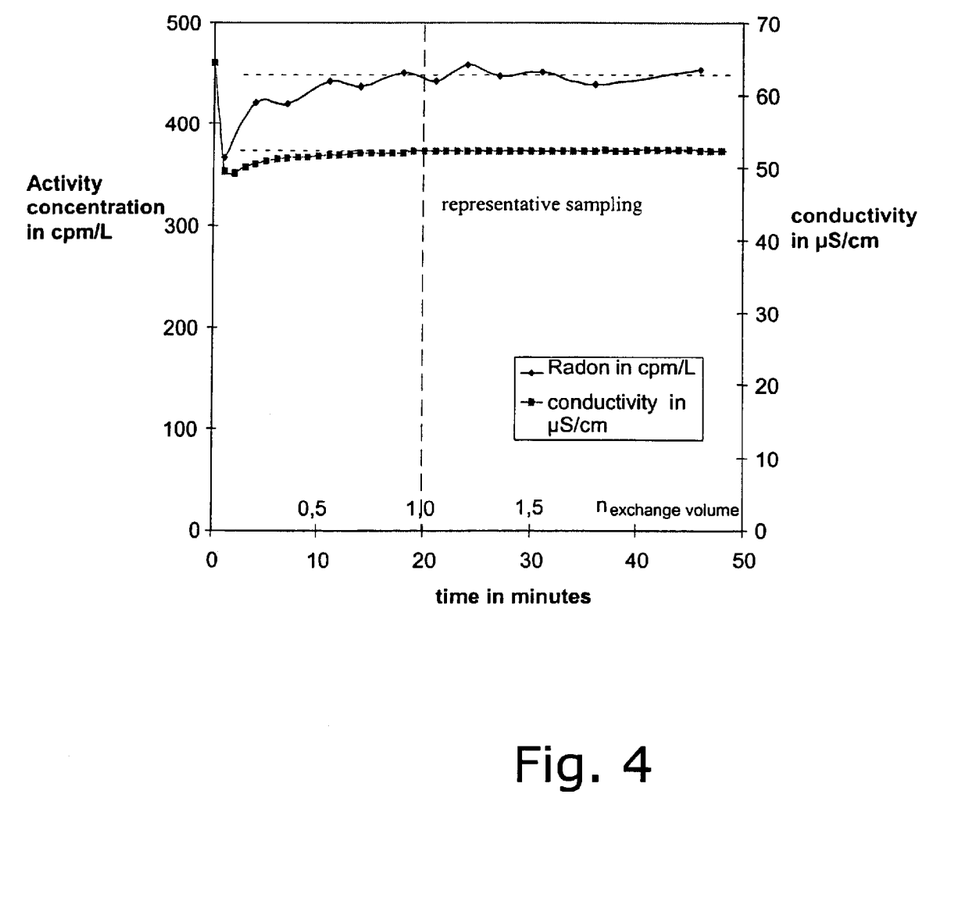

In Experiment B, the pump was installed in the filter region of the second groundwater observation pipe (installed depth 48 m, vertical water column up to the lower edge of the filter 43 m). The gravel fill was 6.5 m thick and the pump output amounted to 1.73 m$^3$/h Samples were taken as in experiment A, the experiment lasting 50 minutes (FIG. 4).

The evaluation revealed that, in the case of experiment A, the whole of the static water in the groundwater observation pipe and in the filtering gravel had to be exchanged before the representative sampling. As expected, the radon activity concentration commenced at zero and increased up to a plateau value of 5,180 cpm/L (FIG. 3). This curve is a reliable measure of the ratio of static water to groundwater in the sample. It was possible to take a representative groundwater sample already after 1.2 exchanges of volume. The electrical conductivity increased clearly before the radon activity concentration increased.

In experiment B, the groundwater was pumped immediately after the pump was switched on. Once again, the ratio of groundwater to static water in the sample could be determined directly from the radon activity concentration. According to this determination, the first sample already contained 82% groundwater. Nevertheless, in the case of this arrangement, static water was mixed in with the groundwater for a longer period of time which, standardized to the exchange volume (an imaginary parameter here), permits representative sampling at 1.0 (plateau of the radon activity concentration at 4470 cpm/L). With this arrangement, the conductivity showed only a slight increase from 30 $\mu$S/cm up to a plateau value of 525 $\mu$S/cm.

With the help of the radon activity concentration, it was possible to make a reliable determination of the time at which a representative sample should be taken from a groundwater observation pipe with pump 4 installed directly below the groundwater surface and from a second groundwater observation with the pump 4 installed in the filter region. Moreover, the relative amplitude change of the radon activity concentration in the two experiments was three times larger than that of the electrical conductivity (100% to 32% in experiment A and 18% to 6% in experiment B).

The measurement of the radon activity concentration during the pumping-out process permits the ratio of groundwater to static water in a groundwater sample to be determined reliably. The cause is the rapid decay of the radon in the static water of a groundwater observation pipe because of its short half-life time in conjunction with the steady emanation of radon in the grain structure of the aquifer. With that, the possibility exists of investigating the pumping-out behavior of groundwater observation pipes generally, regardless of where the pump is installed.

Moreover the radon activity concentration can be used to determine the object-specific pumping-out times for groundwater observations pipes. This appears to be meaningful in those cases, in which there is no clarity concerning the precise pumping-out time and special importance is attached to the result of a water analysis, for example, as proof of the success of a cost-intensive clean-up measure. It would also be conceivable to use the radon activity concentration for groundwater observation pipes of the measurement networks of the Länder, where a high degree of representativeness is required and the costs and benefits are in an excellent ratio to one another. The use of radon activity concentration may also be meaningful for evaluating the operational efficiency of waste groundwater observation pipes. The filters of older groundwater observation pipes become clogged. This affects the hydraulic operational efficiency. No groundwater or only a little groundwater flows through the filter. For evaluating the hydraulic functional efficiency, a scooped sample can be taken from the region of the filter. If the radon activity concentration of this sample is zero, groundwater is no longer flowing through the filter. If, after the scooped sample is taken, a pumping-out experiment is carried out and the radon activity concentration is measured during the pumping-out trial, conclusions concerning the flow through the filter can be drawn from the ratio of the radon activity concentration of the scooped sample to the plateau value of the trial.

In a variation of the invention, it is possible to measure the total activity concentration instead of the radon activity concentration, the radon activity concentration making a large contribution to the total activity concentration and other nuclides with a longer half life not interfering with the method. Likewise, it is possible to measure the radon activity concentration online.

In practice, the in situ determination of the sampling time by online measurement is of decisive importance. When considering the practical applicability of the method, it must be kept in mind that the actual quantitative determination of the radon activity concentration is not as important as the adequacy of the determination of the total activity concentration of the groundwater for the proposed method. This is based therein that radon causes the bulk of the activity and a constant background activity from nuclides having longer half lives does not interfere with the method. Accordingly, there are two possibilities for an online measurement for determining the pumping-out volume of groundwater measurement sites:

a) Direct Measurement of Radon and the Short-Lived Products of its Natural Decay As can be seen from Table 1, the following radionuclides are the short-lived products of the natural decay of radon-222: Po-218, Pb-214, Bi-214 and Po-214.

TABLE 1

Summary of Essential Physical Radiation Properties of Rn-222 and Rn-220 Decay Product

| Isotope | T½ | Radiation | α-Energy (MeV) | γ-Energy (MeV) |
|---|---|---|---|---|
| Ra-226 | 1602 y | α, γ | 4.78 (94.3%) 4.69 (5.7%) | 0.186 (3.3%) |
| Rn-222 | 3.82 d | α | 5.49 (100%) | |
| Po-218 | 3.05 min | α | 6.00 (100%) | |
| Pb-214 | 26.8 min | β, γ | — | 0.295 (19%) 0.352 (36%) |
| Bi-214 | 19.7 min | β, γ | — | 0.609 (47%) 1.120 (15%) |
| Po-214 | 164 ms | α | 7.68 (100%) | |
| Pb-210 | 22.3 y | β | — | 0.0465 (4.06%) |
| Ra-224 | 3.66 d | α | 5.45 (6%) 5.68 (94%) | 0.241 (3.9%) |
| Rn-220 | 55 s | α | 6.29 (100%) | |
| Po-216 | 0.15 s | α | 6.78 (100%) | |
| Pb-212 | 10.6 h | β, γ | — | 0.239 (47%) 0.300 (3.2%) |
| Bi-212 | 60.6 min | α, β, γ | 6.05 (25%) 6.09 (10%) | 0.727 (11.8%) 1.620 (2.8%) |
| Po-212 | 304 ns | α | 8.78 (100%) | |
| Ti-208 | 3.1 min | β, γ | — | 0.511 (23%) 0.583 (86%) 0.860 (12%) 2.614 (100%) |

After the radon is extracted from the water and, with that, separated from these decay products, the daughter nuclide with the longest half life (Pb-214 with $T_{1/2}$= 26.8 minutes) essentially determines the time at which the radioactive equilibrium is reached once again after four half-life times, that is, after about two hours. A rapid measurement of radon is possible by way of an alpha spectrophotometric determination of radon and Po-218 ($T_{1/2}$=3.1 minutes), since the equilibrium between Rn-222 and Po-218 is reached already after about 12 minutes. A different possibility consists therein that an air-filled tube, consisting of a membrane that is permeable by diffusion, is installed in the form of a coil in the stream produced by the pump. The radon diffuses out of the water through the tube into the air and can be measured online in a measurement cell, such as a Lucas cell (SURBECK, 1996). Here there is also an example of an online measurement of radon in tap water with a time resolution of 30 minutes. A further reduction in the measurement time to one minute depends on whether the accuracy, which can still be achieved then, is adequate for the proposed method of determining the pumping-out times.

b) Measurement of the Total Activity Concentration

The possibility exists here of using different measuring equipment and measuring principles, which are already in existence.

For the online detection of guiding characteristic values, a new flow-through measurement cell is provided which, aside from measuring the natural radon activity concentration, also measures the flow rate and the traditional guiding characteristic values, such as electrical conductivity, temperature and pH. All guiding characteristic values are shown and documented online by an appropriate software program as a function of the pumping-out volume. The evaluation of the curves recorded and, in particular, the determination of the plateau values of all guiding parameters, as well as a proposal for an optimum time for taking representative samples also belongs to the operational extent of this software. With such a flow-through measurement cell, sampling from groundwater measuring sites can be objectified, the representativeness of the groundwater samples increased and, at the same time, the pumping-out times reduced, the costs of the sampling thus being lowered.

A further proposed apparatus is a borehole probe for the online detection of guiding characteristic values in groundwater measuring sites.

The unconfined groundwater flow frequently is idealized with the help of the DUPUIT assumption, which states that the flow is horizontal over the whole thickness of the aquifer. Real groundwater, on the other hand, has vertical flow components, which are brought about by small pressure differences in the region of centimeters. With that, the correct design of efficient groundwater measuring sites for a depth-oriented representative sampling is of great importance. If a groundwater measuring site is defective, there is a slow flow through this site between the filter and the defective site (short-circuited flow). For a 4-inch pipe and a pressure difference of only 1 cm in 10 meters, the vertical flow through the measurement site pipe is 100,000 times as great as the horizontal flow through the aquifer. For taking representative samples therefore, it is of particular importance to identify defective groundwater measuring sites.

Flow meter measurements, which can be used if the flow velocities are sufficiently large, are known as methods for measuring short-circuited flows directly. For slow flow velocities, borehole television (optical search for mechanical damage) and temperature measurements are used, which do not always lead to the desired results. For this reason, the new borehole probe for localizing water entry sites in a tubed borehole is proposed. This borehole probe operates on the basis of the natural radon activity concentration in the groundwater.

In static water, the radon activity concentration of a groundwater measuring site is almost zero, because the radon, with its half-life of 3.5 days, decays within a short time. Sites for the entry of groundwater into a measuring site through defective sleeves or torn pipes can be identified by the presence of radon-222 in the static water of the measuring site, even if the flow velocities are very low. If a radon-222 log is carried out at a measuring site, the entry site, the direction of flow and, depending on the flow velocity, also the outlet site of groundwater can be localized (radon-222 is sensitive to groundwater for up to 15 days after entry into the measuring site). This method can be used in tubed boreholes for localizing short-circuited flows through defective sleeves, leaking pipes, non-functioning packers or in repeatedly filtered measuring sites and is also suitable for localizing water entries in boreholes that are not piped. The above-proposed borehole probe measures the radon activity concentration in the static water of a measuring site during an online examination.

For this purpose, for example, a tube, permeable to radon, is immersed, for example, in the form of a coil in the water that is to be sampled. The radon diffuses from the water into the tube, through which air is flowing, the radon concentration of which can then be measured online in a measurement cell (such as a Lucas cell).

There is also the possibility of integrating the radon activity concentration as a new parameter in conventional flow-through measurement cells. Aside from the radon activity concentration, such a flow-through measurement cell is capable of measuring the usual instantaneous parameters, such as the conductivity, the temperature and the pH and, moreover, of realizing an inductive flow-through measurement. By using microelectronic components, all information can be stored, displayed optically online and recorded and, above all, the optimum pumping-out times can be determined reproducibly from the slope of all curves.

The invention is not limited to the examples described here. Rather, by a simple combination of the means and distinguishing features mentioned, it is possible to realize further variations of the embodiments without leaving the scope of the invention.

List of Reference Symbols 1 filtering gravel
1a filter pipe
2 standpipe
3 clay obstruction
4 pump
5 sampling vessel
5a neck
6 inlet pipe
7 bottom of sampling vessel
9 glass attachment
10 venting tube
11 groundwater sample
12 polyethylene tube
13 tube coupling
14 cocktail

What is claimed is:

1. A method for online determination of characteristic values in groundwater measuring sites, comprising the steps of pumping-out an output stream of groundwater at a groundwater measuring site, continuously determining from the output stream parameters identifying natural radon activity concentration and total activity concentration by measuring, electrical conductivity, temperature and pH, comparing the measured parameters relative to a volume measurement taken from the output stream, plotting the values of the parameters online as a function of the pumping-out volume, calculating from said parameters a plateau value of the activity concentration as well as an optimum time for taking a representative sample.

2. The method of claim 1, wherein the measuring of electrical conductivity, temperature and pH is done with a device which comprises an air-filled tube, comprising a membrane, which is permeable by diffusion.

3. The method of claim 2, wherein the tube is constructed in the form of a coil.

* * * * *

UNITED STATES PATENT AND TRADEMARK OFFICE
CERTIFICATE OF CORRECTION

PATENT NO. : 6,498,341 B2
DATED : December 24, 2002
INVENTOR(S) : Dehnert et al.

It is certified that error appears in the above-identified patent and that said Letters Patent is hereby corrected as shown below:

<u>Title page,</u>
Item [62], Related U.S. Application Data, change "Pat. No. 6,252,598" to -- Pat. No. 6,232,598 --.

Signed and Sealed this

Eighteenth Day of March, 2003

JAMES E. ROGAN
*Director of the United States Patent and Trademark Office*